(12) United States Patent
Penn et al.

(10) Patent No.: US 11,926,446 B1
(45) Date of Patent: Mar. 12, 2024

(54) SYSTEM AND METHOD FOR FORMULATING COMPOUNDS INTO PERSONAL CARE PRODUCTS

(71) Applicant: Good Foods Group, LLC, Pleasant Prairie, WI (US)

(72) Inventors: Kurt Penn, Northfield, IL (US); Hannah Penn, Northfield, IL (US); Joyce Longfield, Gurnee, IL (US); Malin Benicek, Middleton, WI (US)

(73) Assignee: Good Foods Group, LLC, Pleasant Prairie, WI (US)

( * ) Notice: Subject to any disclaimer, the term of this patent is extended or adjusted under 35 U.S.C. 154(b) by 0 days.

(21) Appl. No.: 18/336,255

(22) Filed: Jun. 16, 2023

(51) Int. Cl.
| | | |
|---|---|---|
| *B65B 19/00* | (2006.01) | |
| *A45D 34/00* | (2006.01) | |
| *A45D 40/00* | (2006.01) | |
| *A61K 8/92* | (2006.01) | |
| *A61K 8/9789* | (2017.01) | |
| *A61Q 19/00* | (2006.01) | |
| *B65B 31/00* | (2006.01) | |
| *B65B 55/02* | (2006.01) | |

(52) U.S. Cl.
CPC .............. *B65B 55/02* (2013.01); *A45D 34/00* (2013.01); *A45D 40/00* (2013.01); *A61K 8/92* (2013.01); *A61K 8/9789* (2017.08); *A61Q 19/00* (2013.01); *B65B 31/00* (2013.01); *A45D 2200/058* (2013.01); *A61K 2800/10* (2013.01); *A61K 2800/524* (2013.01); *A61K 2800/805* (2013.01); *A61K 2800/87* (2013.01)

(58) Field of Classification Search
USPC .......................................................... 53/425
See application file for complete search history.

(56) References Cited

U.S. PATENT DOCUMENTS

| | | | | |
|---|---|---|---|---|
| 8,919,080 | B2* | 12/2014 | Richter | A23L 3/003 |
| | | | | 53/425 |
| 2007/0122492 | A1* | 5/2007 | Behr | A61K 8/9789 |
| | | | | 424/754 |
| 2015/0010683 | A1 | 1/2015 | Wu et al. | |
| 2018/0298457 | A1 | 10/2018 | Ridenour et al. | |
| 2020/0284347 | A1 | 9/2020 | Lopez Ondevilla et al. | |
| 2022/0047494 | A1* | 2/2022 | Lee | A61K 8/42 |

FOREIGN PATENT DOCUMENTS

| | | |
|---|---|---|
| DE | 102005027811 A1 | 12/2006 |
| WO | 2019229215 A2 | 12/2019 |
| WO | 2022060663 A1 | 3/2022 |

\* cited by examiner

*Primary Examiner* — Chinyere J Rushing-Tucker
(74) *Attorney, Agent, or Firm* — Maier & Maier, PLLC

(57) ABSTRACT

One or more methods for preparing a personal care product using HPP may be provided. The methods may include preparing one or more raw materials, including for example botanical or plant matter. The one or more raw materials may be infused into a substance using HPP, which may result in an infused substance. To make the final personal care product the infused substance may then be mixed with one or more additional ingredients and the personal care product may then be packaged. Finally, before shipping and distribution, the packaged personal care product may be processed using HPP, which may extend the shelf-life of the packaged product.

12 Claims, 3 Drawing Sheets

SYSTEM AND METHOD FOR FORMULATING COMPOUNDS INTO PERSONAL CARE PRODUCTS

BACKGROUND

Topical skin treatments, ointments, lotions, haircare, and other personal care products are popular health products used by many people to treat or maintain skin. Many of these products utilize various plant materials and/or botanical ingredients. Many personal care products contain water or other ingredients that are at risk of microbial growth and cross contamination.

In order to increase the shelf-life of personal care products existing products use various chemical preservatives and stabilizers, however these preservatives and stabilizers may reduce the effectiveness of the product by introducing non-natural ingredients that may be harsh on a user's skin or have other negative health consequences, for example the preservatives may inhibit the growth of natural beneficial bacteria that resides on the user's skin. Additionally, certain ingredients, such as retinol and vitamin C, are particularly prone to destabilization, requiring even higher percentages of preservatives.

Some products have bio-extracts as ingredients, in order to extract the materials to be used in these health products, bioactive compound extraction is commonly used. Generally bioactive compound extraction introduces synthetic ingredients and chemicals into the process and/or uses high temperatures, which may be undesirable for health-centric users and/or degrade the beneficial components of the bio-extracts.

High pressure processing (HPP) is often used in the food industry in order to preserve foods. HPP provides a way of pasteurizing food products without using high temperatures (as is required by normal pasteurization methods). Avoiding high temperatures helps reduce degradation of useful nutrients and compounds in the product undergoing HPP, while still increasing the shelf-life of the product. HPP is dependent on the water content of the food or item being processed, and so has traditionally been used on higher water content food, for example guacamole. HPP uses extreme pressure to kill microorganisms by disrupting the cell membrane or cell wall.

SUMMARY

According to at least one exemplary embodiment, one or more systems and methods for preparing personal care products using HPP may be described. The methods may include preparing one or more raw materials, including for example botanical or plant matter. The one or more raw materials may be extracted and dispersed throughout a substance using HPP, which may result in an infusion. To make the final personal care product the infusion may then be mixed with one or more additional ingredients and the personal care products may then be packaged. Finally, before shipping and distribution, the packaged personal care products may be processed using HPP, which may extend the shelf-life of the packaged product.

The systems may include one or more sealable containers which may each include one or more raw materials and a base substance. There may be a first pressure chamber that one or more sealable containers undergo HPP inside the first pressure chamber. There may further be a refrigerated chamber where the sealable containers are stored for a threshold amount of time after undergoing HPP. In some embodiments there may further be one or more product containers and a second pressure chamber where the one or more product containers may undergo HPP inside the second pressure chamber.

BRIEF DESCRIPTION OF THE FIGURES

Advantages of embodiments of the present invention will be apparent from the following detailed description of the exemplary embodiments. The following detailed description should be considered in conjunction with the accompanying figures in which.

DETAILED DESCRIPTION

Figure 1:
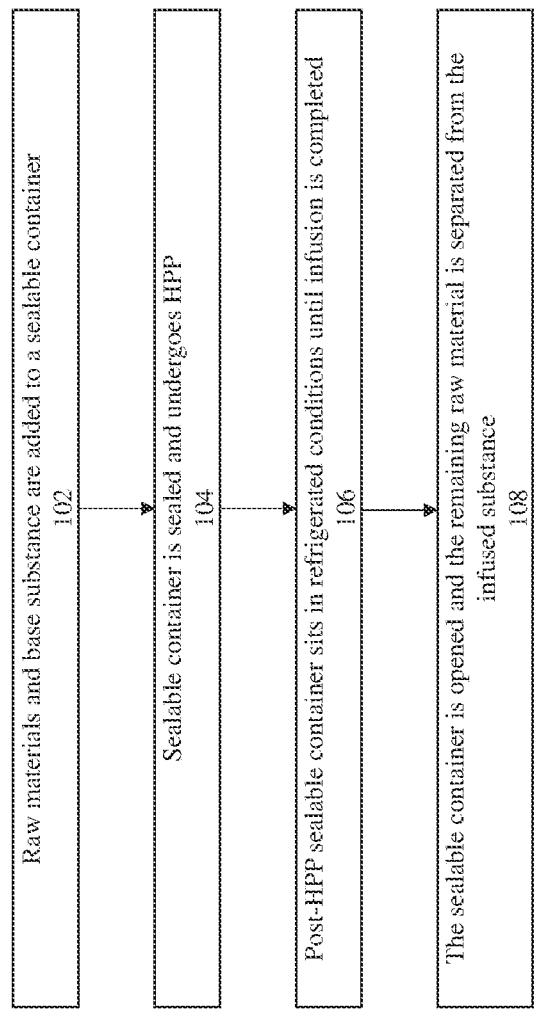
FIG. 1 shows an exemplary method of making an aqueous infusion using HPP.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

As used herein extraction is the process of removing one or more compounds from a raw material and dispersing throughout a base substance. The compounds may be, for example, bio-active compounds, acids, or oils. Examples of the compounds may include, but are not limited to, gallotannin, calcium oxalate, safrole, ursolic acid, carvacrol oil, etc.

As used herein an infusion is the result obtained by the process of extraction, e.g. the resulting water with one or more compounds dispersed throughout.

As used herein, high pressure processing (HPP) may be understood to mean processing goods at high pressures, typically in order to inactivate harmful pathogens and microorganisms by disrupting cell membranes or cell walls. HPP may be understood to be synonymous with ultra-high-pressure processing (UHP), hydrostatic pressure processing (HHP), or high-pressure pasteurization.

As used herein extraction HPP may be understood to mean using HPP for the purpose of extracting one or more compounds from one or more raw ingredients, whereas stabilization HPP may be understood to mean using HPP to process goods in order to inactivate harmful pathogens.

In the following embodiments HPP may involve, for example, introducing one or more sealable containers containing goods that are to be pressurized into a high-pressure chamber. It may be understood that the one or more sealable containers may additionally be flexible, deformable, or otherwise capable of conveying ambient pressure, and may be, for example but not limited to, a pouch, bag, and/or bottle. The sealable container may be made of, for example but not limited to, polymers or plastics, such as polyethylene terephthalate (PET), polyethylene (PE), polypropylene (PP), and/or ethylene-vinyl alcohol copolymer (EVOH). Once the sealable containers are placed in the high-pressure chamber, the high-pressure chamber may be filled with a pressure-transmitting fluid, such as water. It may be understood that the pressure-transmitting fluid may be at or below ambient temperatures. The high-pressure chamber may then be pressurized by, for example, a pump. The pressurization may continue for a specified period of time, for example 2-5 minutes, before the chamber is depressurized.

It may be understood that HPP may be performed at ambient or below ambient temperatures, for example, 40-80° F., or preferably 40-50° F.

In one or more exemplary embodiment a method for extracting compounds for formulation into personal care products without using additional chemicals or synthetic additives may be provided.

FIG. 1 shows an exemplary method of making an infusion using HPP. In a first step 102 raw materials and a base substance may be added to a sealable container. In some embodiments a plurality of raw materials may be added to each container, while in others a single ingredient may be added to each. The base substance may be, for example, an aqueous base, comprising at least one of water, coconut water, etc. In some embodiments the base substance may contain a percentage of an alcohol such as ethanol or isoproponal, which may be used, for example, to extract fat soluble materials. The ethanol or isoproponal concentration may be dependent on the targeted material and may be, for example, approximately 30-50%. The sealable container may be, for example, plastic bags or bottles. The sealable container may be sealed, for example, using a heat seal, or in some embodiments may be a spouted container with a resealable spout. It may be understood that in some embodiments, the sealable container may be reusable. In a next step 104 the sealable container may be sealed and undergo HPP. The HPP may utilize cold water pressure, for example water between 40-50° F., with a pressure of 300-600 MPa or 43,500-87,000 PSI. In other embodiments ambient temperature water, for example between 50-80° F., may instead be used. It may be understood that the pressure during HPP may extract one or more compounds from the raw materials, by providing uniform pressure to the raw material cell membranes, which may allow the raw material to release the desired compound or compounds into the base substance.

In a next step 106 the sealable container may be kept in refrigerated conditions, for example in a 35-45° F. environment, until the extraction has been completed, and the compounds have dispersed throughout the base substance. In some embodiments whether the extraction is completed may be determined as a predetermined amount of time passing, for example at least two weeks, such as two to five weeks, in other embodiments compound testing may be utilized to determine that at least a predetermined concentration of compounds are present in the base substance. It may be understood that in some embodiments the infusion may be tested to verify targeted concentrations. In some embodiments the extraction may be diluted to meet targeted concentrations, for example the extraction may be mixed with water and diluted to 1-30% concentration. In a final step 108 the sealable container may be opened, and the remaining raw material may be separated from the infusion. In some embodiments the remaining raw material may be repurposed, for example by "upcycling" the raw materials for use in other products, by grinding down, pulverizing, drying out, or compositing the used raw materials.

In an exemplary embodiment the process described in FIG. 1 may be utilized where the raw materials are botanical or plant matter, and the base substance is an aqueous base. In this embodiment the raw materials may be, for example, botanical or plant matter such as, but not limited to, whole or sliced cucumber, dried lavender plant, witch hazel, willow bark, sweet potato, etc. Specific raw materials may be selected based on the raw materials exemplary bio-active compounds, in order to generate specific personal care products. Table 1 below shows an exemplary list of raw ingredients and some of their exemplary bio-active compounds.

TABLE 1

| Species | Key Bioactives |
|---|---|
| Witch Hazel | Gallotannin |
| | Calcium Oxalate |
| | Safrole |
| | Carvacrol Oil |
| | Eugenol Oil |
| Calendula officinalis | Patulitrin |
| | Patuletin |
| | Oleanolic Acid |
| | Ursolic Acid |
| Arnica montana | Acid |
| | polysaccharides |
| | Sesquiterpene |
| | Lactone |
| | Thymol |
| | Flavonoids |
| Willow Bark w/Coffee | Salicin |
| | Chlorogenic Acid |
| | Caffeine |
| | Phenolics |
| Reishi Mushrooms | Triterpenoids |
| | Polysaccharides |
| | Amino acids-Lysine |
| | and Leucine |
| Papaya | Vitamin C |
| | Lycopene |
| Sweet Potato | Beta-carotene/Vit A |
| | Anthocyanins |
| | Pantothenic acid |
| Coconut cream | Fatty acids |
| | Polyphenols |
| Coconut yogurt | Fatty acids |
| | Polyphenols |
| Coconut water | Vitamin C |
| Aloe Vera | Antioxidants |
| | Vitamin A |
| | Vitamin C |
| Oats | Phenols |
| Blueberry | Vitamin E |
| | Vitamin C |
| | Beta-carotene/Vitamin A |
| Kiwi | Vitamin C |
| | Vitamin E |
| | Vitamin K |
| | Potassium |
| | Folate |
| | Essential fatty acids |
| | Omega-6 type |
| | (linoleic acid) and |
| | Omega-3 (alpha-linolenic acid) |
| Cucumber | Flavonoids |
| | Lignans |
| | Triterpenes |

TABLE 1-continued

| Species | Key Bioactives |
| --- | --- |
| Banana | B-Vitamins |
|  | Vitamin A |
|  | Vitamin E |
|  | Zinc |
|  | Lectin |
| Pineapple | Bromelain (enzyme) |
|  | Vitamin C |
|  | Vitamin B |
|  | Vitamin E |
|  | Flavonoids |
|  | Phenolic acid |
|  | Alpha hydroxy acid(s)-Citric |
| Orange | Vitamin A |
|  | Vitamin B |
|  | Vitamin C |
|  | Folate |
|  | Phytochemicals |
|  | Flavonoids |
| Rice flour | Ferulic Acid |
|  | Allantoin |
| Lemon | Alpha hydroxy acids-Citric acid |
|  | Vitamin C |
| Grapefruit | Alpha hydroxy acids-Citric, Tartaric and Malic |
|  | Vitamin C |
| Black carrot | Beta-carotene/Vitamin A |
|  | Lutein |
|  | Vitamin C |
| Blue Majik seaweed (Spirulina) | gamma-Linolenic acid |
| Dulse seaweed (red) | Iodine |
|  | Beta-carotene/Vitamin A |
| Walnut | Omega-3 (alpha-linolenic acid) |
| Pomegranate seed oil | Omega-5 Fatty Acids-(Punicic acid) |
|  | Vitamin C |
|  | Anthocyanins |
|  | Ellagic acid |
|  | Tannin |
| Rice bran oil | Omega-3 (alpha-linolenic acid) |
|  | Omega-9 (Erucic, Oleic) |
|  | gamma oryzanol |
|  | Tocotrienol(s) |
| Grapeseed oil | Omega-3 (alpha-linolenic acid) |
|  | Proanthocyanidins |
|  | Pycogeneol |
|  | Tocopherol |
| Sunflower seed oil | Omega-3 (alpha-linolenic acid) |
|  | Omega-9 (Erucic, Oleic) |
|  | Sesamol |
|  | Vitamin E |
| Manuka honey | Methylglyoxal |
|  | Glucose oxidase (enzyme) |
| Ginger | >40 antioxidants |
| CBD oil |  |
| Rose hip oil | Omega-3 (alpha-linolenic acid) |
|  | Omega-6 type (linoleic acid) |
| Mint oil | Rosmarnic acid |
|  | Eriocotrin |
|  | Luteolin |
|  | Hesperidin |
|  | Methanol/Menthone |
| Prickly pear oil | Omega-9 (Erucic, Oleic) |
|  | Omega-3 (alpha-linolenic acid) |
|  | Vitamin E |
|  | Vitamin K |
|  | Betalains |
| Frankincense | Boswellic acid |
| Bergamont oil | Linalool |
| Lavender |  |
| Chamomile | Bisabolol |
|  | Chamazulene |
| Tumeric | Curcumin |
| Hyaluronic acid |  |
| Vitamin E oil | Vitamin E |

The method may extract one or more bioactive compounds from the botanical or plant matter and disperse the extracted compounds through the aqueous base. It may be understood that in some embodiments some of the compounds extracted may act as natural alternatives to chemical preservatives. The extracted compounds may include, but are not limited to, antioxidants, vitamins, minerals, enzymes, fibers, sugars, acids, and/or oils.

Figure 2:
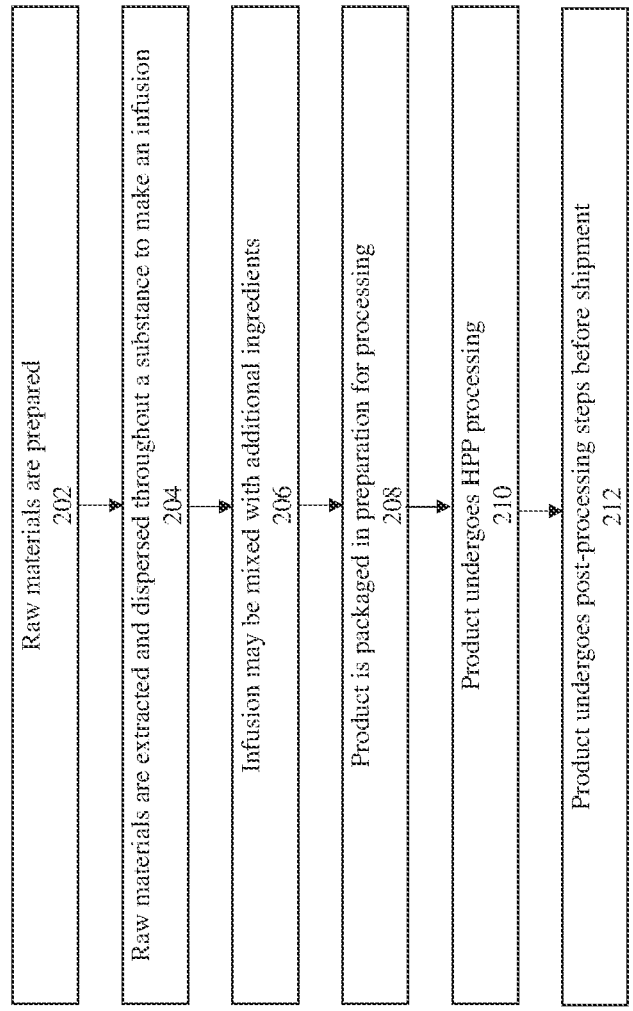
FIG. 2 shows an exemplary method for creating a personal care product utilizing HPP.

FIG. 2 shows an exemplary method for creating a personal care product utilizing HPP 200 without the use of preservatives and stabilizers. In a first step 202, raw materials may be prepared. Raw materials may include, for example, botanical or plant matter such as, but not limited to, whole or sliced cucumber, dried lavender plant, witch hazel, willow bark, sweet potato, etc. and/or oils and vitamins such as mint oil, CBD oil, vitamin e oil, grapeseed oil, etc. In a next step 204 the raw materials may be extracted and dispersed through an aqueous base in order to make an infusion. In some embodiments the extraction process may be, for example, the method described above in FIG. 1. In a next step 206, the infusion may optionally be mixed with a variety of additional ingredients, some of which may be refrigerated ingredients. It may be understood that in some embodiments this step is unnecessary as the infusion itself may be the final personal care product. Mixing the infusion with the additional ingredients may include, for example, chopping, mixing, blending, and/or homogenizing, for example by running the mixture through a shear pump. In some embodiments the infusion and/or additional ingredients may first be weighed in order to specifically determine the ratio of ingredients to be mixed. In some embodiments the infusion from step 204 may itself be the product. In a next step 208 the mixed product may be packaged in preparation for processing. The packaging may be, for example but not limited to, single use pods, airless pump applicators or bottles, or other containers. In some embodiments the packaging may also be filled with a modified atmosphere such as nitrogen or carbon dioxide, such as when the product in question has ingredients with oxidative sensitivity.

In a next step 210 the packaging may be hermetically sealed and undergo HPP. The HPP may utilize cold water pressure, for example water between 40° F.-50° F., with a pressure of 300-600 MPa or 43,500-87,000 PSI. In other embodiments ambient temperature water, for example between 50° F.-80° F., may instead be used. In some embodiments the packaging may go directly into the pressure chamber of the HPP system. In a final step 212 the product may undergo any post-processing steps necessary to finish preparation for distribution or sale. For example, but not limited to, code dating, quality assurance tests, case packing, etc. For example, in an exemplary embodiment the product may be packed in cups sealed with film and packed into cartons. The finalized product may be kept in refrigerated conditions which may extend the shelf-life of the final product without the need for adding preservatives or stabilizers. The refrigerated condition may be, for example 32-41° F., or preferably 36-40° F.

Figure 3:
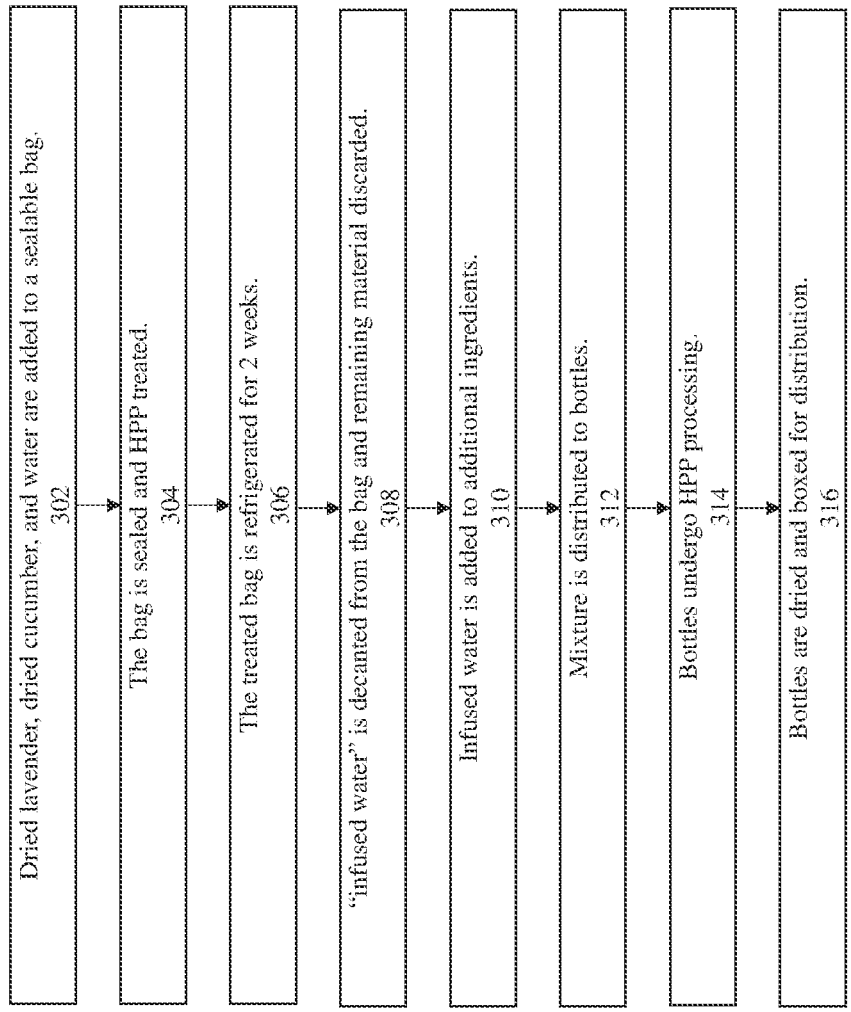
FIG. 3 shows an exemplary cosmetic composition utilizing the described method.

FIG. 3 shows an exemplary cosmetic composition utilizing the described method 300. It may be understood that the composition may be free of preservatives and stabilizers and therefore may be considered all natural. The following is just one example and may be understood to be illustrative of the method described above. In a first step 302, dried lavender, dried cucumber, and water may be added to a sealable bag. In a next step 304 the bag may be sealed and undergo HPP treatment as described in step 104 above. In a next step 306 the HPP treated bag may be refrigerated for, for example, 2 weeks. After the refrigeration it may be understood that the water has become "infused water".

In a next step 308 the sealable bag may be unsealed, and the "infused water" may be decanted, while the remaining raw material may be discarded or otherwise repurposed. In a next step 310 the infused water may be added to additional ingredients, for example the extraction may be diluted and then mixed with glycerin, agave, a surfactant, an oil, shea butter, niacinamide, and/or xantham gum in order to make a cleanser. In a next step 312 the cleanser may be distributed to a plurality of bottles, which may be flexible in order to support HPP processing. In a next step 314 the bottles may directly undergo HPP processing. In a final step 316 the bottles may be dried and boxed for final distribution.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method for preparing a personal care product using HPP, comprising:
   preparing one or more raw materials;
   extracting and dispersing one or more compounds from the one or more raw materials using HPP to make an infusion;
   packaging a personal care product, wherein the personal care product includes at least the infusion; and
   processing the packaged personal care product using HPP;
   wherein after extracting the one or more extracted compounds into a base substance, leaving the base substance and raw materials in a refrigerated environment for at least a threshold amount of time, wherein the threshold amount of time is at least 2 weeks.

2. The method for preparing the personal care product of claim 1, further comprising mixing the infusion with one or more additional ingredients before packaging the personal care product.

3. The method for preparing the personal care product of claim 1, wherein the threshold amount of time is a time until the base substance contains a predetermined concentration of extracted compounds.

4. The method for preparing the personal care product of claim 1, wherein the one or more raw materials include at least botanical or plant matter, the base substance is an aqueous base, and the substance is an infused liquid.

5. The method of preparing the personal care product of claim 4, wherein the extracted compound is at least one of antioxidants, vitamins, minerals, enzymes, fibers, sugars, acids, and oils.

6. The method of preparing the personal care product of claim 4, wherein the botanical or plant matter includes at least one of whole or sliced cucumber, dried lavender plant, witch hazel, willow bark, or sweet potato.

7. The method of preparing the personal care product of claim 4, wherein the aqueous base is at least one of water and coconut water.

8. The method of preparing the personal care product of claim 1, further comprising placing the raw materials and base substance in a sealable container prior to extraction.

9. The method of preparing the personal care product of claim 1, wherein the HPP is performed at 40-80° F. and at 300-600 MPa of pressure.

10. The method of preparing the personal care product of claim 9, wherein the HPP is performed at 40-50° F.

11. The method of preparing the personal care product of claim 1, wherein the personal care product is packaged in one of a single use pod, an airless pump applicator, or an airless bottle.

12. The method of preparing the personal care product of claim 11, further comprising adding a modified atmosphere to the personal care product packaging.

\* \* \* \* \*